United States Patent
Tiwari et al.

(10) Patent No.: US 9,597,393 B2
(45) Date of Patent: Mar. 21, 2017

(54) SYNTHETIC TOLL-LIKE RECEPTOR-4 (TLR-4) AGONIST PEPTIDES

(71) Applicant: AV Therapeutics, Inc., New York, NY (US)

(72) Inventors: Raj Tiwari, Bellerose, NY (US); Robert Suriano, Cliffside Park, NJ (US); Abraham Mittelman, Scarsdale, NY (US); Jan Geliebter, Brooklyn, NY (US)

(73) Assignee: AV THERAPEUTICS, INC., New York, NY (US)

( * ) Notice: Subject to any disclaimer, the term of this patent is extended or adjusted under 35 U.S.C. 154(b) by 0 days.

(21) Appl. No.: 14/377,782

(22) PCT Filed: Feb. 11, 2013

(86) PCT No.: PCT/US2013/025568
§ 371 (c)(1),
(2) Date: Aug. 8, 2014

(87) PCT Pub. No.: WO2013/120073
PCT Pub. Date: Aug. 15, 2013

(65) Prior Publication Data
US 2015/0017202 A1  Jan. 15, 2015

Related U.S. Application Data

(60) Provisional application No. 61/597,069, filed on Feb. 9, 2012.

(51) Int. Cl.
*G01N 33/53* (2006.01)
*A61K 39/02* (2006.01)
*A61K 39/39* (2006.01)
*G01N 33/92* (2006.01)
*A61K 39/00* (2006.01)

(52) U.S. Cl.
CPC .......... *A61K 39/39* (2013.01); *A61K 39/0011* (2013.01); *A61K 39/02* (2013.01); *G01N 33/5308* (2013.01); *G01N 33/92* (2013.01); *A61K 2039/55516* (2013.01); *A61K 2039/6081* (2013.01); *G01N 2405/00* (2013.01); *G01N 2500/04* (2013.01)

(58) Field of Classification Search
None
See application file for complete search history.

(56) References Cited

U.S. PATENT DOCUMENTS

| 7,592,421 B1 | 9/2009 | Ferrone et al. |
| 2006/0018919 A1 | 1/2006 | Gu |
| 2008/0014209 A1* | 1/2008 | Rice ..................... A61K 39/095 424/185.1 |

OTHER PUBLICATIONS

Ishizaka et al. Expert Rev. Vaccines 6: 773-784, 2007.*
Brade, L. et al., "Immunization with an anti-idiotypic antibody against the broadly lipoplysaccharide-reactive antibody WNI 222-5 induces *Escherichia coli* R3-core-type specific antibodies in rabbits", Innate immunity (2011), vol. 18:2, pp. 279-293.
Field, S.K. et al., "An anti-idiotype antibody which mimics the inner-core region of lipopolysaccharide protects mice against a lethal challenge with endotoxin", Infection and Immunity (1994), vol. 62:9, pp. 3994-3999.
Kato, T. et al., "Protection of Mice against the Lethal Toxicity of a Lipopolysaccharide (LPS) by Immunization with Anti-Idiotype Antibody to a Monoclonal Antibody to Lipid A from Eikenella corrodens LPS", Infection and Immunity (1990), vol. 58:2, pp. 416-420.
Shanmugam, A. et al. "Synthetic Toll Like Receptor-4 (TLR-4) Agonist Peptides as a Novel Class of Adjuvants", PLos ONE (2012), vol. 7:2, pp. e30839 (10 pgs.).
Shanmugam, A. et al., "LPS Mimotopes: A Novel Class of TLR4", Cancer Research (2011), vol. 71:8; Abstract 5396, 2 pgs.
Anti-*E. coli* J5 LPS Monoclonal Antibody (2D7/1), published on the AntibodyShop (http://www.theantibodyshop) downloaded Jun. 5, 2013, 3 pgs.

* cited by examiner

*Primary Examiner* — S. Devi
(74) *Attorney, Agent, or Firm* — Andrews Kurth Kenyon LLP

(57) ABSTRACT

The invention provides novel immunological adjuvants and methods for identification of such adjuvants. The invention further provides methods and compositions for eliciting an immune response to an immunogen using the novel adjuvants. The adjuvants can be employed with any suitable immunogen, including proteins, peptides, lipids, and carbohydrates. The immunogen can be derived from a virus, a cancer, or a diseased cell. The elicited immune response can be cellular, humoral, or both.

7 Claims, 10 Drawing Sheets

SEQUENCE LISTING

<160> NUMBER OF SEQ ID NOS: 13

<210> SEQ ID NO 1
<211> LENGTH: 7
<212> TYPE: PRT
<213> ORGANISM: Artificial Sequence
<220> FEATURE:
<223> OTHER INFORMATION: synthetic peptide

<400> SEQUENCE: 1

Gln Glu Ile Asn Ser Ser Tyr
1               5

<210> SEQ ID NO 2
<211> LENGTH: 7
<212> TYPE: PRT
<213> ORGANISM: Artificial Sequence
<220> FEATURE:
<223> OTHER INFORMATION: synthetic peptide

<400> SEQUENCE: 2

Ser His Pro Arg Leu Ser Ala
1               5

```
<210> SEQ ID NO 3
<211> LENGTH: 7
<212> TYPE: PRT
<213> ORGANISM: Artificial Sequence
<220> FEATURE:
<223> OTHER INFORMATION: synthetic peptide

<400> SEQUENCE: 3

Ser Met Pro Asn Pro Met Val
1               5

<210> SEQ ID NO 4
<211> LENGTH: 7
<212> TYPE: PRT
<213> ORGANISM: Artificial Sequence
<220> FEATURE:
<223> OTHER INFORMATION: synthetic peptide

<400> SEQUENCE: 4

Gly Leu Gln Gln Val Leu Leu
1               5

<210> SEQ ID NO 5
<211> LENGTH: 7
<212> TYPE: PRT
<213> ORGANISM: Artificial Sequence
<220> FEATURE:
<223> OTHER INFORMATION: synthetic peptide

<400> SEQUENCE: 5

His Glu Leu Ser Val Leu Leu
1               5

<210> SEQ ID NO 6
<211> LENGTH: 7
<212> TYPE: PRT
<213> ORGANISM: Artificial Sequence
<220> FEATURE:
<223> OTHER INFORMATION: synthetic peptide

<400> SEQUENCE: 6

Tyr Ala Pro Gln Arg Leu Pro
1               5

<210> SEQ ID NO 7
<211> LENGTH: 7
<212> TYPE: PRT
<213> ORGANISM: Artificial Sequence
<220> FEATURE:
<223> OTHER INFORMATION: synthetic peptide

<400> SEQUENCE: 7

Thr Pro Arg Thr Leu Pro Thr
1               5

<210> SEQ ID NO 8
<211> LENGTH: 7
<212> TYPE: PRT
<213> ORGANISM: Artificial Sequence
<220> FEATURE:
<223> OTHER INFORMATION: synthetic peptide

<400> SEQUENCE: 8

Ala Pro Val His Ser Ser Ile
1               5
```

```
<210> SEQ ID NO 9
<211> LENGTH: 7
<212> TYPE: PRT
<213> ORGANISM: Artificial Sequence
<220> FEATURE:
<223> OTHER INFORMATION: synthetic peptide

<400> SEQUENCE: 9

Ala Pro Pro His Ala Leu Ser
1               5

<210> SEQ ID NO 10
<211> LENGTH: 7
<212> TYPE: PRT
<213> ORGANISM: Artificial Sequence
<220> FEATURE:
<223> OTHER INFORMATION: synthetic peptide

<400> SEQUENCE: 10

Thr Phe Ser Asn Arg Phe Ile
1               5

<210> SEQ ID NO 11
<211> LENGTH: 7
<212> TYPE: PRT
<213> ORGANISM: Artificial Sequence
<220> FEATURE:
<223> OTHER INFORMATION: synthetic peptide

<400> SEQUENCE: 11

Val Val Pro Thr Pro Pro Tyr
1               5

<210> SEQ ID NO 12
<211> LENGTH: 7
<212> TYPE: PRT
<213> ORGANISM: Artificial Sequence
<220> FEATURE:
<223> OTHER INFORMATION: synthetic peptide

<400> SEQUENCE: 12

Glu Leu Ala Pro Asp Ser Pro
1               5

<210> SEQ ID NO 13
<211> LENGTH: 15
<212> TYPE: PRT
<213> ORGANISM: Artificial Sequence
<220> FEATURE:
<223> OTHER INFORMATION: synthetic peptide

<400> SEQUENCE: 13

Gly Gln Trp Gln Ser Gly Asp Arg Tyr Trp Met Glu Thr Ser Thr
1               5                   10                  15
```

SYNTHETIC TOLL-LIKE RECEPTOR-4 (TLR-4) AGONIST PEPTIDES

CROSS-REFERENCE TO RELATED APPLICATIONS

This application claims priority to U.S. Application No. 61/597,069, filed Feb. 9, 2012, which is incorporated herein by reference in its entirety.

FIELD OF THE INVENTION

The invention concerns methods and compositions for inducing an antigenic or immunogenic response in a subject.

BACKGROUND OF THE INVENTION

Lipopolysaccharide (LPS) is the major structural component of gram negative bacteria and is composed of three distinct domains; lipid A, a core oligosaccharide chain, and an O-antigen. Of the three LPS domains discussed, the O-antigen is most variable and distinguishes among various gram negative bacterial strains. Importantly, LPS is recognized by the immune system during infection. It is this recognition and interaction between LPS and the immune system, specifically the innate branch of the immune system, which leads to a potentially life threatening condition known as sepsis. Septic shock remains the number one cause of death in intensive care units and is responsible for 750,000 new cases with 250,000 of these new cases resulting in death within the U.S. Death by septic shock is attributed to the inflammatory cytokines released by members of the innate immune system, such as antigen presenting cells (APC), which ultimately leads to dysfunction and failure of the body's major organ systems.

Inflammatory cytokine secretion occurs upon the initial interaction between LPS and its receptor, toll-like receptor 4 (TLR-4), present on antigen presenting cells (APCs) such as macrophages and dendritic cells. TLR-4 belongs to a family of transmembrane receptors, which are responsible for recognizing and responding to pathogen associated molecular patterns (P AMPS) such as LPS. Upon activation of TLR-4, a series of signal transduction events occur ultimately leading to nuclear translocation of transcription factor NF-KB, subsequently resulting in transcription of various inflammatory cytokines such as TNF-α, IL-1β, and IL-12p70. Collectively, these inflammatory cytokines are responsible for the systemic inflammatory response syndrome observed during septic shock. Although responsible for causing systemic inflammation, the inflammatory response associated with LPS may be beneficial if the signal transduction initiated by LPS, which is similar to that observed in adjuvants, can be optimally regulated.

Adjuvants are substances that accelerate and/or enhance an antigen specific immune response. The purpose of an adjuvant is to make an antigen visible to the eyes (macrophages/dendritic cells) of the immune system. Recognition of antigens by APCs essentially initiates the critical cascade of events leading to localized inflammation, which recruits APCs and ultimately leads to initiation of a productive cell mediated and/or antibody mediated immune response. Although various adjuvants exist, not all are approved for human use and the adjuvants which are approved are associated with adverse side effects such as malaise and inflammation. Currently, the majority of human vaccines contain aluminum salts as an adjuvant and pharmaceutical companies are developing oil-based adjuvants to be incorporated into vaccines. Another class of adjuvants which is gaining interest is toll-like receptor (TLR) agonists. Currently, adjuvants which act as agonists to TLR-2, TLR-5, TLR7/8, and TLR-9 are being studied, and one TLR-4 agonist, monophosphoryl lipid A, is FDA approved. Although promising, many of these agonists are bacterial molecules.

SUMMARY OF THE INVENTION

The present invention provides LPS mimics, including a new class of synthetic TLR-4 agonist adjuvants. The LPS mimics eliminate the need for adjuvants such as bacterial proteins and lipids. Phage display libraries that can be used to developed peptide and non-peptide such synthetic TLR-4 agonists. According to the invention, peptides are identified that functionally mimic LPS, for example, by inducing nuclear translocation of NF-κB. Further, like LPS, the peptide mimics cause release of various inflammatory cytokines that are released upon activation by the LPS.

Accordingly, the invention provides a method of identifying an immunological adjuvant, which comprises isolating a compound that binds to an anti-lipopolysaccharide (LPS) antibody or antigen binding fragment thereof, and testing the compound for activation of NF-κB, wherein activation of NF-κB indicates that the compound is an immunological adjuvant. In an embodiment of the invention, the anti-LPS antibody binds to the lipopolysaccharide core. In another embodiment of the invention, the anti-LPS antibody binds to lipid A. In certain embodiments of the invention, the anti-LPS antibody blocks LPS binding to a toll-like receptor. In certain embodiments, the antibody blocks binding to a toll-like receptor 4 complex or a component of that complex. In an embodiment of the invention, the toll-like receptor is TLR-4, whose function involves the adaptor molecule MD-2 and CD14. In an embodiment of the invention, the antibody is 2D7/1.

The immunological adjuvants of the invention activate NF-κB. In an embodiment of the invention, activation of NF-κB is indicated by nuclear localization. In another embodiment of the invention, activation of NF-κB is indicated by secretion of one or more inflammatory cytokines from an antigen presenting cell (APC), such as, but not limited to, a macrophage or a dendritic cell. In an embodiment of the invention, activation of NF-κB is indicated by expression of a reporter gene under NF-κB control.

According to the invention, the adjuvant can be a peptide, which can be composed of L amino acids, D amino acids, or combinations thereof. In an embodiment of the invention, the adjuvant peptide is 30 amino acids or less in length. In one such embodiment, the adjuvant peptide is from 4 to 10 amino acids in length. In another embodiment, the adjuvant peptide is from 7 to 15 amino acids in length. In an embodiment of the invention, the adjuvant peptide is 6, 7, 8, or 9 amino acids in length.

Accordingly, the invention provides an isolated peptide that binds to an anti-lipopolysaccharide (LPS) antibody or antigen binding fragment thereof and activates NF-κB. In an embodiment of the invention, the adjuvant peptide comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or a sequence at least 70%, or at least 80%, or at least 85%, or at least 90% similar thereto. In another embodiment of the invention, the adjuvant peptide consists essentially of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or a sequence at least 70%, or at least 80%, or at least 85%, or at least 90% similar thereto. In another embodiment of the invention, the adjuvant peptide consists of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or a sequence at least 70%, or at least 80%, or at least 85%, or at least 90% similar thereto.

The invention provides a method of inducing an immune response, which comprises administering an immunogen and an adjuvant peptide to a subject in an amount effective to produce an immune response therein, wherein the adjuvant peptide was obtained by a method which comprises identifying a compound that specifically binds to an anti-lipopolysaccharide (LPS) antibody or antigen binding fragment thereof, and activates NF-κB. In an embodiment of the invention, the adjuvant peptide comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or a sequence at least 70%, or at least 80%, or at least 85%, or at least 90% similar thereto. In another embodiment of the invention, the adjuvant peptide consists essentially of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or a sequence at least 70%, or at least 80%, or at least 85%, or at least 90% similar thereto. In another embodiment of the invention, the adjuvant peptide consists of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or a sequence at least 70%, or at least 80%, or at least 85%, or at least 90% similar thereto. In an embodiment of the invention, the immunogen is a conjugate with a carrier protein.

The invention also provides a method of enhancing a protective immune response to an immunogen, comprising administering the immunogen and an adjuvant peptide to a subject in an amount effective to produce an immune response therein, wherein the adjuvant peptide was obtained by a method which comprises identifying a compound that binds to an anti-lipopolysaccharide (LPS) antibody or antigen binding fragment thereof, and activates NF-κB. In an embodiment of the invention, the adjuvant peptide comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or a sequence at least 70%, or at least 80%, or at least 85%, or at least 90% similar thereto. In another embodiment of the invention, the adjuvant peptide consists essentially of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or a sequence at least 70%, or at least 80%, or at least 85%, or at least 90% similar thereto. In another embodiment of the invention, the adjuvant peptide consists of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or a sequence at least 70%, or at least 80%, or at least 85%, or at least 90% similar thereto. In an embodiment of the invention, the immunogen is a conjugate with a carrier protein.

The invention further provides a method of making an immunogenic composition comprising combining an immunogen and an adjuvant peptide in amounts effective to produce an immune response against the immunogen in a subject, wherein the adjuvant peptide was obtained by a method which comprises identifying a compound that specifically binds to an anti-lipopolysaccharide (LPS) antibody or antigen binding fragment thereof, and activates NF-κB. The invention also provides an immunogenic composition comprising an immunogen and an adjuvant peptide in amounts effective to produce an immune response against the immunogen in a subject, wherein the adjuvant peptide was obtained by a method which comprises identifying a compound that binds to an anti-lipopolysaccharide (LPS) antibody or antigen binding fragment thereof, and activates NF-κB. In an embodiment of the invention, the adjuvant peptide comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or a sequence at least 70%, or at least 80%, or at least 85%, or at least 90% similar thereto. In another embodiment of the invention, the adjuvant peptide consists essentially of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or a sequence at least 70%, or at least 80%, or at least 85%, or at least 90% similar thereto. In another embodiment of the invention, the adjuvant peptide consists of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or a sequence at least 70%, or at least 80%, or at least 85%, or at least 90% similar thereto.

DETAILED DESCRIPTION

Figure 1:
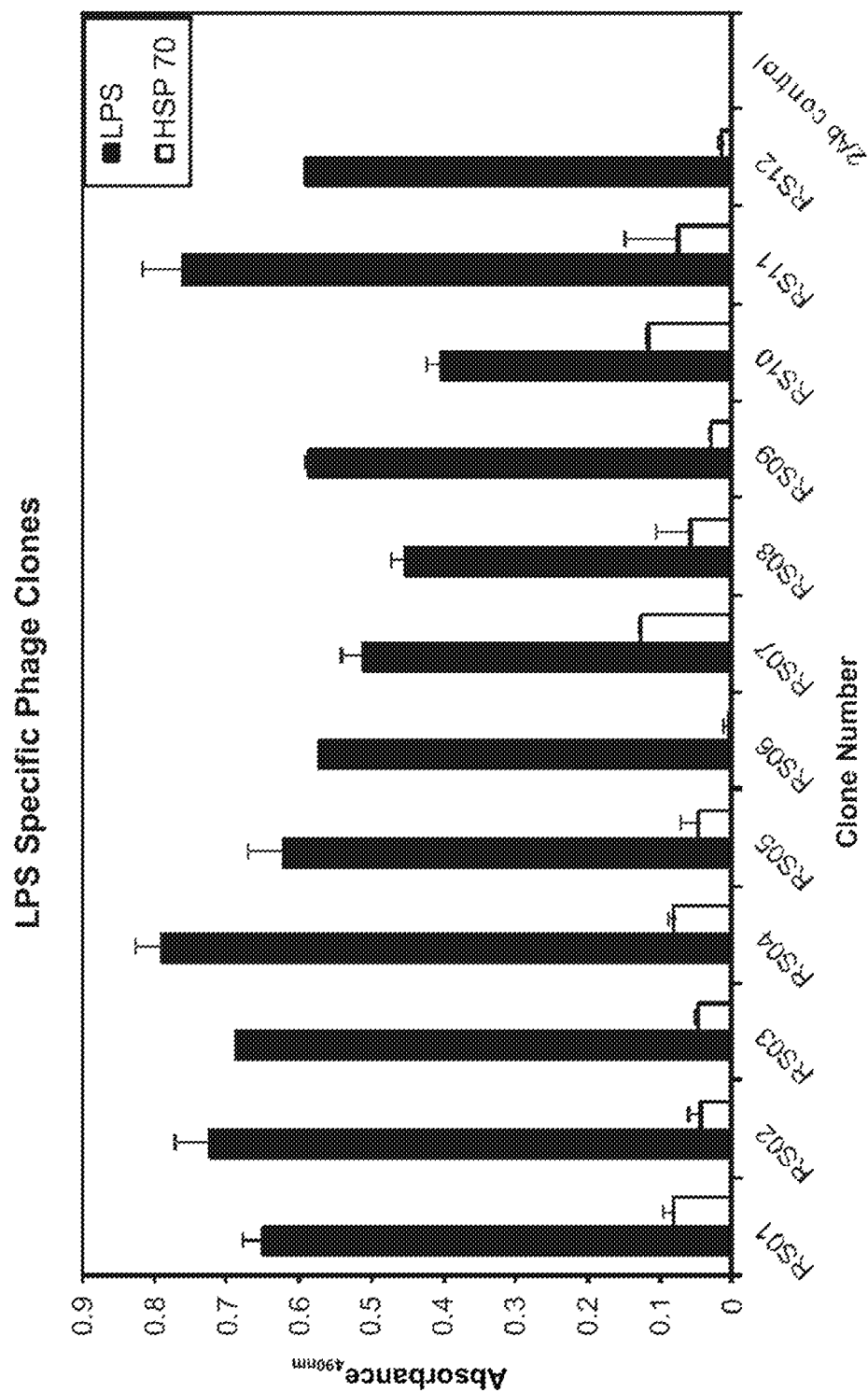
FIG. 1—Identification of LPS specific peptide mimotopes. LPS antibody was immobilized at a concentration of 1 µg per well of a 96-well plate. Phages ($2\times10^{11}$) expressing 7-mer peptides were initially added to the well of a 96-well plate containing immobilized LPS antibody after which non-specific phages were removed. Twelve phage clones were selected from three rounds of panning and specificity to LPS antibody (black bars) was confirmed by ELISA using HSP70 antibody (white bars) as a negative control. All 12 (RS01-RS12) clones selected displayed specific reactivity to LPS antibody, as determined using the HRP labeled anti-M13 phage antibody which was detected by the HRP substrate SIGMAFAST™ OPD and absorbance measured at 490 nm. Each experiment was repeated three times with similar results observed. The standard deviation shown above each sample represents three replicates in one experiment.

The invention provides novel adjuvants and methods for identification of such adjuvants. In preferred embodiments, the adjuvants can be synthesized directly, and need not be obtained or purified from living organisms. In particular, the invention provides compounds that mimic structural and/or NF-κB activating properties of bacterial lipopolysaccharide (LPS). Such mimics can be obtained from, e.g., synthetic libraries of compounds, and identified on the basis that they bind to agents that bind to LPS. As exemplified herein, an agent that binds to LPS is an antibody.

LPS is a uniquely bacterial glycolipid. It consists of three structurally distinct domains; lipid A, the membrane anchor and endotoxic portion of LPS; the core saccharide consisting of a branched chain of nonrepeating hexose and heptose sugars; and the O-antigen side chain, a repeating unit of sugars that extends into the extracellular milieu. The core can be further divided into the outer core (semivariable composition of sugars and linkages among bacterial species and strains) and the inner core (considerably conserved among bacterial species and strains). The polysaccharide region is anchored in the outer bacterial membrane by lipid A. The most active form of lipid A contains six fatty acyl groups and is found in pathogenic bacteria such as *Escherichia coli* and *Salmonella* species.

According to the invention, immunological adjuvants can be identified by their ability to bind to agents that bind to LPS. In certain embodiments, the immunological adjuvants bind to agents that bind to LPS core. In certain embodiments, the immunological adjuvants bind to agents that bind to lipid A. According to the invention, agents that bind to LPS, LPS core, and/or lipid A can be antibodies, which can be monoclonal or polyclonal, and be from any mammal, including without limitation, mouse, rat, rabbit, sheep, goat, and human, or obtained from a non-animal source, such as an antibody library. The anti-LPS antibodies can be obtained by any method, including, for example, by immunization of a mammal with whole bacteria or an extract thereof, or by screening a library of antibodies or antigen binding fragments thereof.

While much work with endotoxin has been done with species of *E. coli* and *Salmonella*, anti-LPS antibodies can be obtained using a variety of organisms. For example, antibodies can be obtained from individuals immunized with a polyvalent O serotype LPS vaccine, or with "rough" mutant bacteria lacking any O serotype LPS polysaccharide and expressing only the common core glycolipid (CGL) region of the LPS molecule. In certain embodiments, the anti-LPS antibodies can be to a "cocktail' of LPS from a mixture of gram-negative bacteria or to lipid A. The anti-LPS antibodies can be any isotype. In one embodiment, the anti-LPS antibody is IgG. In another embodiment, the anti-LPS antibody is IgM. In another embodiment, the antibodies are a mixture of isotypes.

Antibody 2D7/1 is exemplified and is available from a variety of commercial sources (e.g., Abcam, Cambridge, Mass., cat# ab35654; Acris Antibodies, Herford, Germany, cat# BM1091; Thermo Fisher/Pierce cat# MA1-83152). Antibody 2D7/1 was obtained by immunizing mice with untreated whole *E. coli* J5 cells. *E. coli* strain J5 is a genetically stable UDG-4-epimerase-deficient $R_C$ mutant that was derived from *E. coli* 0111:B4, and is unable to attach oligosaccharide side chains ("O" or somatic antigens) to the core oligosaccharide-lipid A complex (common core antigens). Subsequent immunizations were a combination of a pool of untreated whole bacterial cells (*E. coli* J5, *Pseudomonas aeruginosa, Proteus mirabilis*, and *Salmonella typhimurium*) plus a pool of 4 LPS (from *E. coli, Pseudomonas aeruginosa, Proteus mirabilis*, and *Salmonella minnesota* 595). The antibody also reacts with *K. pneumoniae, S. sonnei* and *S. typhimurium*. In an embodiment of the invention, an anti-LPS antibody used to identify an immunological adjuvant competes with binding of antibody 2D7/1 to LPS.

Adjuvants are usually identified according to the invention by generating libraries of compounds and screening for desired binding and/or adjuvant characteristics. As exemplified, the agents that bind to LPS are antibodies, and the adjuvants are peptides, but the methods and examples disclosed are generally applicable to any epitope library. In an embodiment of the invention, peptides to be screened are encoded by filamentous phage and expressed as part of a phage coat protein. The technique of phage display is well known in the art, and allows for amplification of the library and multiple rounds of screening.

Immunological adjuvants screened and identified by the method can be relatively short, and are generally 30 amino acids or less. The adjuvants are preferably from 4 to 10 amino acids, or from 7 to 15 amino acids. In certain embodiments, the peptides are 6, 7, 8, or 9 amino acids in length. The adjuvant peptides can have flexible or constrained secondary structures. The flexibility of linear peptides is constrained, for example, by incorporation of proline or by disulfide bonds formed between cysteine residues.

Other types of libraries may also be employed, for example, any sort of synthetic polymers that can be screened and their structure or sequence determined. Numerous methods have been devised for generation of chemical diversity and mass screening of libraries. To simplify identification of library elements of interest, many libraries have the feature that synthesis steps are encoded. For example, in phage display, the displayed peptide is encoded in the genome encapsulated by the phage particle. Amino acid sequences of peptides identified by screening procedures are easily determined by sequencing a small predetermined part of the genome.

In another example, peptides can be generated in numbers several orders of magnitude greater than by conventional one-at-a-time methods by synthesis on polyethylene rods or pins, arranged, for example, in a microtiter plate format. The pin technology is representative of techniques that generate libraries of single compounds in a spatially-differentiated manner. That is, the structure or sequence of a binding substance identified in a binding assay would be known based on its location in an array of binding substances. An alternative approach to rapidly prepare large mixtures of compounds, is the split-pool approach (e.g., Houghten, R. A., 1985, *Proc. Natl. Acad. Sci. U.S.A.* 82:5131-5135) where a solid support material (e.g., beads) is physically segregated into equal portions for coupling to each of the individual initial reactants. This affords uniform coupling since competition between reactants is eliminated. The individual polymers are combined in a single vessel for washing and deprotection and then divided again into individual portions for the next coupling. Using this approach, a complete set of possible molecular combinations is rapidly prepared in approximately equimolar amounts. Coincident with coupling reactions, "identifier" tags can be attached to the solid support material. The structure of the molecule on any bead identified through screening is obtained by decoding the identifier tags. Numerous methods of tagging the beads have now been reported.

Thus, alternatives to peptide libraries include polymers of peptide-like and small organic molecules. In one non-limiting example, a polymer library uses a collection of N-substituted glycines as peptide monomers, which are assembled in a modular fashion. (Zuckermann, R. N. et al, 1994, *J. Med. Chem.* 37:2678-2685.) The structures of the resulting compounds are unique, display unique binding properties, and incorporate the important functionalities of peptides in a novel backbone. Furthermore, studies suggest this class of compounds is resistant to enzymatic breakdown. According to one such embodiment, an adjuvant of the invention consists of, or comprises, D-amino acids.

According to the invention, useful adjuvant peptides activate NF-κB. In its inactivated state, NF-κB is located in the cytosol complexed with the inhibitory protein IκBα. Extracellular signals activate NF-κB by causing its dissociation from IκBα. The activated NF-κB is then translocated into the nucleus where it binds to specific sequences of DNA called response elements (RE). Accordingly, one indication of NF-κB activation is nuclear localization. Assays to monitor nuclear localization are well know in the art. As exemplified herein, nuclear localization can be monitored by assaying nuclear and cytoplasmic protein fractions of test cells for NF-κB levels. Alternatively, NF-κB nuclear translocation can be monitored visually by labeling NF-κB and observing localization in the nucleus. In certain embodiments, the nucleus is identified by DAPI staining. TLR-mediated activation of NF-κB can also be determined using cells transiently or stably transfected to express TLR-4, the adaptor molecule MD-2, and CD14. NF-κB activation can be detected using an NF-κB-driven reporter gene construct. A variety of NF-κB-driven reporter gene vectors are commercially available, using reporter genes such as luciferase, green fluorescent protein, red fluorescent protein, and others. In certain embodiments, the peptides can be shown to bind to a TLR-4 complex.

According to the invention, adjuvant peptides induce secretion of pro-inflammatory cytokines and related proteins. Thus, adjuvant peptides of the invention are identified by induction of secretion of macrophage inflammatory protein-1α (MIP-1α), macrophage inflammatory protein-1γ (MIP-1γ), interleukin-1α (IL-1α), interleukin-4, (IL-4), interleukin-6 (IL-6), interleukin-12 (i.e., the activated heterodimer IL-12p70), RANTES, tumor necrosis factor (TNF; TNF-α, cachexin), monocyte chemotactic protein-1 (MCP-1), soluble tumor necrosis factor receptor I (sTNFRI), soluble tumor necrosis factor receptor II (sTNFRII), macrophage colony-stimulating factor (M-CSF), granulocyte colony-stimulating factor (G-CSF), granulocyte-macrophage colony-stimulating factor (GM-CSF), or combinations thereof.

Non-limiting examples of adjuvant peptides are provided. The invention provides an isolated polypeptide which comprises SEQ ID NO: 1, 2, 3, 4, 5, 6, 7, 8, 9, 10, 11, 12, or an amino acid sequence at least 50%, or at least 60%, or at least 70%, or at least 85%, or at least 90% similar thereto, and activates NF-κB. In another embodiment, the invention provides an isolated polypeptide which consists essentially of SEQ ID NO: 1, 2, 3, 4, 5, 6, 7, 8, 9, 10, 11, 12, or an amino acid sequence at least 50%, or at least 60%, or at least 70%, or at least 85%, or at least 90% similar thereto, and activates NF-κB. In another embodiment, the invention provides an isolated polypeptide which consists of SEQ ID NO: 1, 2, 3, 4, 5, 6, 7, 8, 9, 10, 11, 12, or an amino acid sequence at least 50%, or at least 60%, or at least 70%, or at least 80%, or at least 85%, or at least 90% similar thereto, and activates NF-κB. In certain embodiments, an isolated peptide comprises, consists essentially of, or consists of a sequence that is at least 70%, or at least 85% identical to SEQ ID NO: 1, 2, 3, 4, 5, 6, 7, 8, 9, 10, 11, or 12. "Substantially identical" means an amino acid sequence that which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein. Preferably, the amino acid sequence is at least 80%, more preferably at least about 85%, and most preferably at least about 90% similar to another amino acid sequence. Methods and computer programs for determining sequence similarity are publically available, including, but not limited to, the GCG program package (Devereux et al., Nucleic Acids Research 12: 387, 1984), BLASTP, BLASTN, and FASTA (Altschul et al, J. Mol. Biol. 215:403 (1990). The well-known Smith Waterman algorithm may also be used to determine similarity. The BLAST program is publicly available from NCBI and other sources (BLAST Manual, Altschul, et al., NCBI NLM NIH, Bethesda, Md. 20894; BLAST 2.0 at www.ncbi.nlm.nih.gov/blastO. In comparing sequences, these methods account for various substitutions, deletions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

Immunogenic compositions comprising adjuvants of the invention may be administered to a subject using either a protein or nucleic acid vaccine so as to produce in the subject, an amount of the selected immunogen which is effective in inducing a therapeutic immune response against the target antigen in the subject. The subject may be a human or nonhuman subject. Animal subjects include, without limitation, non-human primates, dogs, cats, equines (horses), ruminants (e.g., sheep, goats, cattle, camels, alpacas, llamas, deer), pigs, birds (e.g., chicken, turkey quail), rodents, and chirodoptera. Subjects can be treated for any purpose, including without limitation, eliciting a protective immune response, or producing antibodies (or B cells) for collection and use for other purposes.

The adjuvants of the invention can be used with any suitable immunogen. As used herein, the term "immunogen" refers to any substance that can be recognized by the immune system (e.g., bound by an antibody or processed so as to elicit a cellular immune response) under appropriate conditions. Without limitation, suitable immunogens include proteins, peptides, polysaccharides, lipids, glycoproteins, lipoproteins, and lipopolysaccharides. In certain embodiments, the immunogen is from an infectious agent (e.g., a virus, bacteria, *Mycobacterium*, fungus or parasite), a plant antigen, cancer, or an allergenic agent. In an embodiment of the invention, the immunogen is a human antigen.

In certain embodiments, an immunogen of interest is expressed by diseased target cells (e.g., neoplastic cell, infected cells), and expressed in lower amounts or not at all in other tissue. Examples of target cells include cells from a neoplastic disease, including but not limited to sarcoma, lymphoma, leukemia, a carcinoma, melanoma, carcinoma of the breast, carcinoma of the prostate, ovarian carcinoma, carcinoma of the cervix, colon carcinoma, carcinoma of the lung, glioblastoma, and astrocytoma. Alternatively, the target cell can be infected by, for example, a virus, a mycoplasma, a parasite, a protozoan, a prion and the like. Accordingly, an immunogen of interest can be from, without limitation, a human papilloma virus (see below), a herpes virus such as herpes simplex or herpes zoster, a retrovirus such as human immunodeficiency virus 1 or 2, a hepatitis virus, an influenza virus, a rhinovirus, respiratory syncytial virus, cytomegalovirus, adenovirus, *Mycoplasma pneumoniae*, a bacterium of the genus *Salmonella, Staphylococcus,* *Streptococcus, Enterococcus, Clostridium, Escherichia, Klebsiella, Vibrio, Mycobacterium*, amoeba, a malarial parasite, and *Trypanosoma cruzi*.

In addition to tumor antigens and antigens of infectious agents, mutants of tumor suppressor gene products including, but not limited to, p53, BRCA1, BRCA2, retinoblastoma, and TSG101, or oncogene products such as, without limitation, RAS, WNT, MYC, ERK, and TRK, may also provide target antigens to be used according to the invention. The target antigen can be a self antigen, for example one associated with a cancer or neoplastic disease. In an embodiment of the invention, the immunogen is a peptide from a heat shock protein (hsp)-peptide complex of a diseased cell, or the hsp-peptide complex itself.

In certain embodiments of the invention, an immunogen is used to elicit an immune response against a self-antigen that is expressed in a developmental or gender specific manner. For example, a host may be tolerized to a self-antigen that normally is expressed at an early stage of development. When that antigen is aberrantly expressed at another point in time, it can be an ideal target of an immune response. In another example, a target antigen of interest may be present in normal tissue of one sex, but not the other. This method further applies where a target antigen is expressed in diseased tissue, but normal tissue of the same cell type has been removed from the host. For example, following prostatectomy, any prostate specific protein is a potential target antigen for eliciting an immune response directed against metastatic cells from a prostate cancer, because normal host tissue that would be targeted by the immune response has already been removed. The invention is also applicable where a target antigen is expressed in relatively large amounts in diseased cells, and small amounts in normal cells. In such an embodiment, an immune response is elicited that is effective against cells expressing the target antigen in large amounts (e.g., having a dense population of a cell surface antigen), but that has little or no effect on cells expressing the target antigen in small amounts.

In certain embodiments, an adjuvant of the invention is used to elicit or enhance an immune response directed to an antigenic determinant of an immunogen that is not normally the target of a major immune response in a host (i.e., an antigenic determinant that is not immunodominant). For example, sharing epitopes of high similarity with the host's molecules would provide a means for escaping immune surveillance. The tolerance mechanisms used to prevent autoimmune destruction would then provide a basis through which tumor-associated antigens and antigens associated with infectious agents escape from functional antigen-specific immune recognition. Such an epitope, which is not normally the target of an immune response, can also provide a means for a virus to escape an immune response directed to a non-essential epitope. That is, for an immunodominant epitope of a virus that is non-essential, the virus can escape an immune response by mutating the immunodominant epitope. Further, virus epitopes associated with essential viral functions may be subdominant and less likely the target of an immune response.

For example, human papilloma viruses (HPV) are viruses of low immunogenicity. Studies have demonstrated that the proliferation and malignant phenotype of human cervical carcinoma cell culture depends on continuous expression of HPV oncogenes E6 and E7, but those tumor antigens are poor immunogens. In another example, while the genomes of HIV-1 isolates are highly variable, they also contain relatively conserved regions which are structurally or functionally important. The conserved regions are not immunologically inert, but the epitopes contained tend to be less immunodominant (i.e., subdominant) than more variable epitopes in natural infection. In an embodiment of the invention, an adjuvant of the invention is used to elicit or enhance an immune response directed to a subdominant epitope of an infectious agent or tumor antigen.

In certain embodiments, the immunogen may be purified from a natural source, obtained by means of recombinant expression, or synthesized directly. In certain embodiments, the immunogen can be provided by whole cells, microorganisms, or viral particles, which may be live, attenuated, or killed. In other embodiments, the immunogen may comprise a protein fragment comprising one or more immunogenic regions of the molecule.

Immunogens include those that are modified or derivatized, such as by conjugation or coupling to one or more groups to enhance an immune response of the subject. Examples of immunogenic carrier proteins are KLH and BSA Immunogenic carriers also include polypeptides that are promiscuous Class II activators (see, e.g., Panina-Bordignon et al., 1989). Conjugate linkages are made by methods well known to those of skill in the art.

In addition to immunogenic proteins and polypeptides, which may comprise a T cell epitope, carriers can also be constructs to which other immunogenic moieties (e.g., cytokines, polypeptides bearing T cell epitopes, etc.) can be linked. Branched constructs such as lipo-thioester and branched polylysine allow for multiple covalent linkages of such immunogenic moieties as well as conjugation of multiple polysialic acid polymers. Carriers further include proteins and polypeptides which have been modified by the covalent addition of immunogenically active moieties. Alternatively, the peptide immunogens can be incorporated into longer sequences of amino acids. The additional sequences can, for example, confer a desired function, such as the ability to bind to a heat shock protein. In certain embodiments, tandem arrays will be produced that comprise multiple copies of one peptide immunogen or comprise multiple peptide immunogens.

Immunogenic compositions of the invention comprise an immunogen and an adjuvant peptide, and can be administered for therapeutic and/or prophylactic purposes. In therapeutic applications, an immunogenic composition of the invention is administered in an amount sufficient to elicit an effective immune response to treat a disease or arrest progression and/or symptoms. The dosage of the adjuvants of the invention will vary depending on the nature of the immunogen and the condition of the subject, but should be sufficient to enhance the efficacy of the immunogen in evoking an immunogenic response. For therapeutic or prophylactic treatment, the amount of adjuvant administered may range from 0.05, 0.1, 0.5, or 1 mg per kg body weight, up to about 10, 50, or 100 mg per kg body weight or more. The adjuvants of the invention are generally non-toxic, particularly by comparison to adjuvants from natural sources, and generally can be administered in relatively large amount without causing life-threatening side effects.

Immunogenic compositions of the invention may further comprise coadjuvants, which generally promote nonspecific immune responses. Representative coadjuvants include aluminum salts (alum), such as aluminum hydroxide, aluminum phosphate, aluminum sulfate, oil-in-water emulsion formulations (e.g., complete and incomplete Freund's adjuvant), Bacille Calmette-Guerin, BCG, and saponin adjuvants, such as QS-21, which comprises a homogeneous saponin purified from the bark of *Quillaja saponaria*, and IL-12 and derivatives. Additional examples of coadjuvants include CpG oligodeoxynucleotides (synthetic oligodeoxynucleotide containing unmethylated CpG dinucleotides), MPL (from the lipopolysaccharide of *Salmonella minnesota* Re595), liposomes, and polymer microspheres made from, e.g., poly(lactic-co-glycolic acid) (PLGA), polyphosphazene or polyanhydrides.

The term "therapeutic immune response", as used herein, refers to an increase in humoral and/or cellular immunity, as measured by standard techniques, which is directed toward the target antigen. Preferably, the induced level of immunity directed toward the target antigen is at least four times, and preferably at least 16 times the level prior to the administration of the immunogen. The immune response may also be measured qualitatively, wherein by means of a suitable in vitro or in vivo assay, an arrest in progression or a remission of a neoplastic or infectious disease in the subject is considered to indicate the induction of a therapeutic immune response.

In the methods of the present invention, a composition comprising an immunogen and an adjuvant of the invention, combined in therapeutically effective amounts, is administered to a mammal in need thereof. The term "administering" as used herein means delivering the immunogen and adjuvant of the present invention to a mammal by any method that may achieve the result sought. They may be administered, for example, intravenously or intramuscularly. The term "mammal" as used herein is intended to include, but is not limited to, humans, laboratory animals, domestic pets and farm animals. "Therapeutically effective amount" means an amount of the immunogen and adjuvant that, when administered to a mammal, is effective in producing the desired therapeutic effect.

Compositions comprising immunogens and adjuvants of the invention may be administered cutaneously, subcutaneously, intravenously, intramuscularly, parenterally, intrapulmonarily, intravaginally, intrarectally, nasally or topically. The composition may be delivered by injection, orally, by aerosol, or particle bombardment.

Compositions for administration may further include various additional materials, such as a pharmaceutically acceptable carrier. Suitable carriers include any of the standard pharmaceutically accepted carriers, such as phosphate buffered saline solution, water, emulsions such as an oil/water emulsion or a triglyceride emulsion, various types of wetting agents, tablets, coated tablets and capsules. Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients. The composition of the invention may also include suitable diluents, preservatives, solubilizers, emulsifiers, adjuvants and/or carriers. Such compositions may be in the form of liquid or lyophilized or otherwise dried formulations and may include diluents of various buffer content (e.g., Tris-HCl, acetate, phosphate), pH and ionic strength, additives such as albumin or gelatin to prevent absorption to surfaces, detergents (e.g., TWEEN® 20, TWEEN® 80, Pluronic F68, bile acid salts), solubilizing agents (e.g. glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexing with metal ions, or incorporation of the material into or onto particulate preparations of polymeric compounds such as polylactic acid, polyglycolic acid, hydrogels, etc. or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

It is to be understood and expected that variations in the principles of invention herein disclosed may be made by one skilled in the art and it is intended that such modifications are to be included within the scope of the present invention.

Throughout this application, various publications are referenced. These publications are hereby incorporated into this application by reference in their entireties to more fully describe the state of the art to which this invention pertains. The following examples further illustrate the invention, but should not be construed to limit the scope of the invention in any way.

EXAMPLES

Example 1

Phage Display

Lipopolysaccharide (LPS) or endotoxin is an integral part of the outer membrane of Gram-negative bacteria. While the "O" antigens are heterogeneous, the common core antigens possess striking chemical, structural, and immunologic homology across strains, species and genera of Gram-negative bacteria. Identification of the LPS peptide mimics was performed by using a 7-mer phage display peptide library referred to as Ph.D.-7 (New England BioLabs, Ipswich, Mass.). Panning was performed according to manufactures specifications using a LPS specific antibody as the target. The LPS antibody used for the panning was a monoclonal antibody, designated 2D7/1 (Abcam, Cambridge, Mass., CAT# ab35654), which was produced by vaccinating mice with whole *Escherichia coli* 0111:B4 J5 cells. *Escherichia coli* strain J5 is a genetically stable UDG-4-epimerase-deficient Rc mutant that was derived from *E. coli* 0111:B4. *Escherichia coli* J5 is a rough mutant that is unable to attach the oligosaccharide side chain ("O" or somatic antigens) to the core oligosaccharide-lipid A complex (common core antigens) associated with the outer membrane of all Gram-negative bacteria. The J5 mutant retains the core LPS containing lipid A, N acetyl glucosamine, 2-keto-3-deoxyoctonate, heptose and glucose (a composition similar to that of the Rc strains of *Salmonella*).

Briefly, 1 μg of the LPS antibody was absorbed to one well of a 96 well plate in a total volume of 100 μl of PBS overnight at 4° C. Phage ($2 \times 10^{11}$) were added to the well and allowed to adhere at room temperature after which non-binding phages were washed away and bound phage eluted. Eluted phage were then amplified and used for further panning so as to enrich for LPS antibody specific phage. The panning procedure described was repeated three times. Twelve random phage clones were selected from three rounds of panning and specificity to LPS antibody (black bars) was confirmed by ELISA using HSP70 antibody (ENZO Life Sciences, Farmingdale, N.Y.) (white bars) as a negative control. The species for both the anti-LPS and anti-HSP70 antibodies used were mouse. Bound phage were detected by using a HRP labeled anti-M13 phage antibody (Abcam) followed by adding the HRP substrate SIGMA-FAST™ OPD (Sigma, St. Louis, Mo.) and absorbance measured at 490 nm using a microplate reader (Bio-Rad, Hercules, Calif.). The panning, titer determination, and ELISA experiments were performed according to the manufacturer's protocol. Once their reactivity was determined, the DNA encoding the peptide sequence from each positively reacting phage clone was purified using QIAprep Spin M13 Kit (Qiagen, Valencia, Calif.) and sequenced by Genewiz (Genewiz, South Plainfield, N.J.) using the primers supplied in the kit (New England BioLabs). The LPS peptide mimics sequenced were synthesized by Genemed Synthesis and their purity was greater than 95% (Genemed Synthesis, San Antonio, Tex.).

TABLE 1

TLR-4 Specific Peptide Sequences

| Phage Clone | Peptide Sequence | SEQ ID NO: |
|---|---|---|
| RS01 | Gln Glu Ile Asn Ser Ser Tyr | 1 |
| RS02 | Ser His Pro Arg Leu Ser Ala | 2 |
| RS03 | Ser Met Pro Asn Pro Met Val | 3 |
| RS04 | Gly Leu Gln Gln Val Leu Leu | 4 |
| RS05 | His Glu Leu Ser Val Leu Leu | 5 |
| RS06 | Tyr Ala Pro Gln Arg Leu Pro | 6 |
| RS07 | Thr Pro Arg Thr Leu Pro Thr | 7 |
| RS08 | Ala Pro Val His Ser Ser Ile | 8 |
| RS09 | Ala Pro Pro His Ala Leu Ser | 9 |
| RS10 | Thr Phe Ser Asn Arg Phe Ile | 10 |
| RS11 | Val Val Pro Thr Pro Pro Tyr | 11 |
| RS12 | Glu Leu Ala Pro Asp Ser Pro | 12 |

Example 2

LPS Peptide Mimics Stimulate TLR-4 and Activate HEK-BLUE™ Cells

The twelve peptides were assayed for their ability to bind to TLR-4 and activate NF-κB using a transgenic HEK293 cell line known as HEK-BLUE™-4. This cell line is stably transfected to only express TLR-4 on its plasma membrane, with no other TLRs present. Detecting activation of NF-κB is made possible by placing secreted alkaline phosphatase (SEAP) under the control of the NF-κB promoter. Therefore, NF-κB activation leads to SEAP secretion, which is detected by an alkaline phosphatase substrate in cell culture media.

The LPS peptide mimics were dissolved in endotoxin free water (HyClone) at a concentration of 1 μg/ml with the exception of peptide 4 which was dissolved in a solution of 1% DMSO made in endotoxin free water at 1 μg/ml concentration. All of the peptide stock solutions and stored at −80° C. Each of the 12 peptides (RS01-RS12) was added to 96-well plates in triplicate in a total volume of 20 μl. The total volume required in each•well was made up with endotoxin free water (HyClone). $5 \times 10^4$ HEK-BLUE™-4 cells (Invivogen, San Diego, Calif.) were added per well and incubated for approximately 20 h after which the supernatant from each well was collected and placed into a new 96-well plate. 180 μl of HEK-BLUE™ detection media (Invivogen), alkaline phosphatase detection substrate, was added to each well and incubated for 1-3 h at 37° C. After a noticeable color change, the absorbance was taken at 630 nm using the microplate reader (Bio-Rad).

Figure 2A:
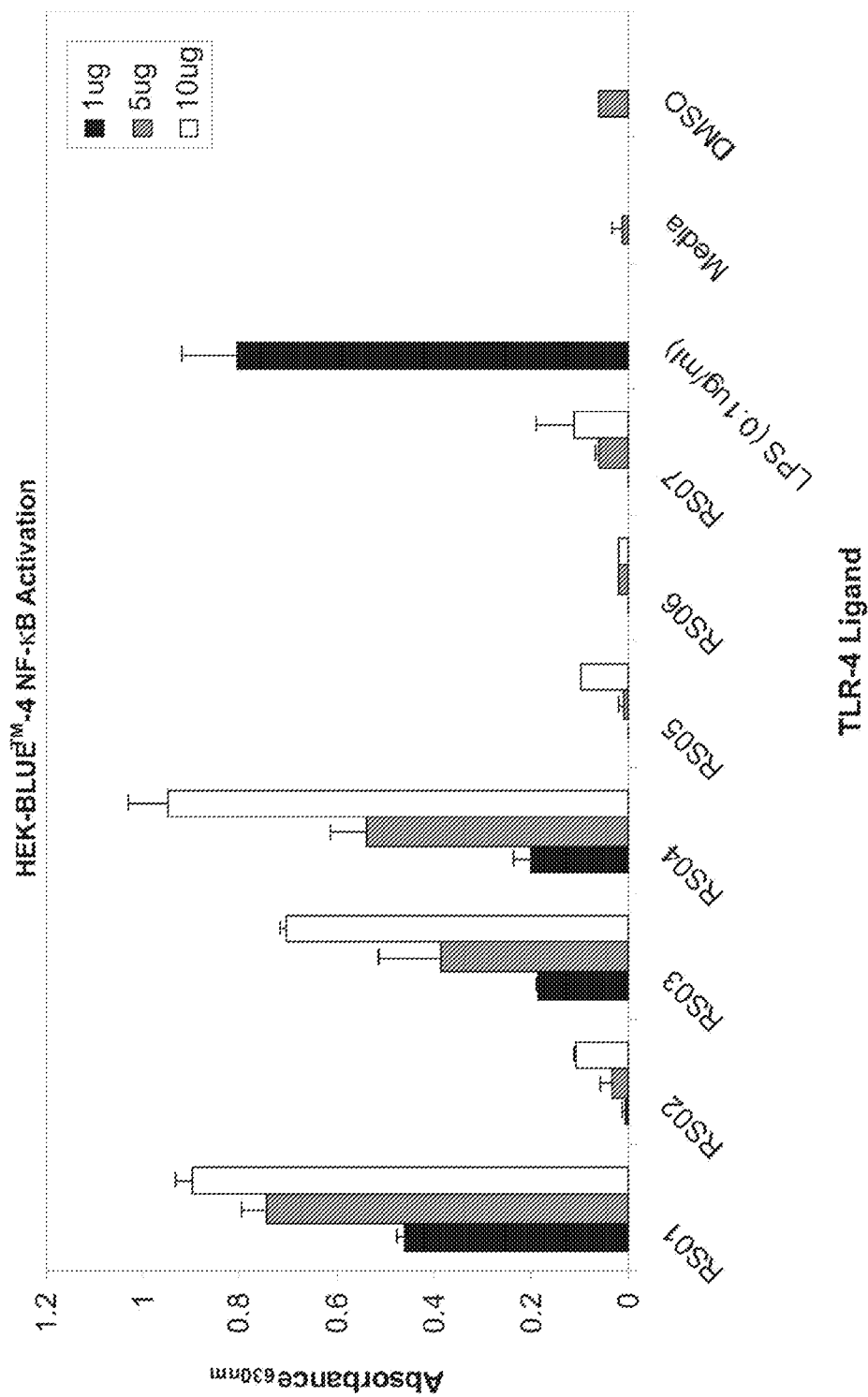
FIG. 2—LPS peptide mimics activate NF-κB in HEK-BLUE™-4. LPS peptide mimics were dissolved in endotoxin free water and added to 96-well plates at three concentrations; 1 µg/ml (black bar), 5 µg/ml (gray bar), and 10 µg/ml (white bar). HEK-BLUE™4 were then added to each well at a concentration of $5\times10^4$ cells per well in complete media. The supernatant was then harvested after 24 h and assayed for alkaline phosphatase secretion indicating activation of NF-κB. NF-κB activation is represented in FIG. 2A for peptides RS01-RS07 and in FIG. 2B for peptides RS08-RS12. LPS was used as a positive control in assaying all peptides for NF-κB activation. Absorbance was taken at 630 nm. Each experiment was repeated three times with similar results observed. The standard deviation shown above each sample represents three replicates in one experiment.
Figure 2B:
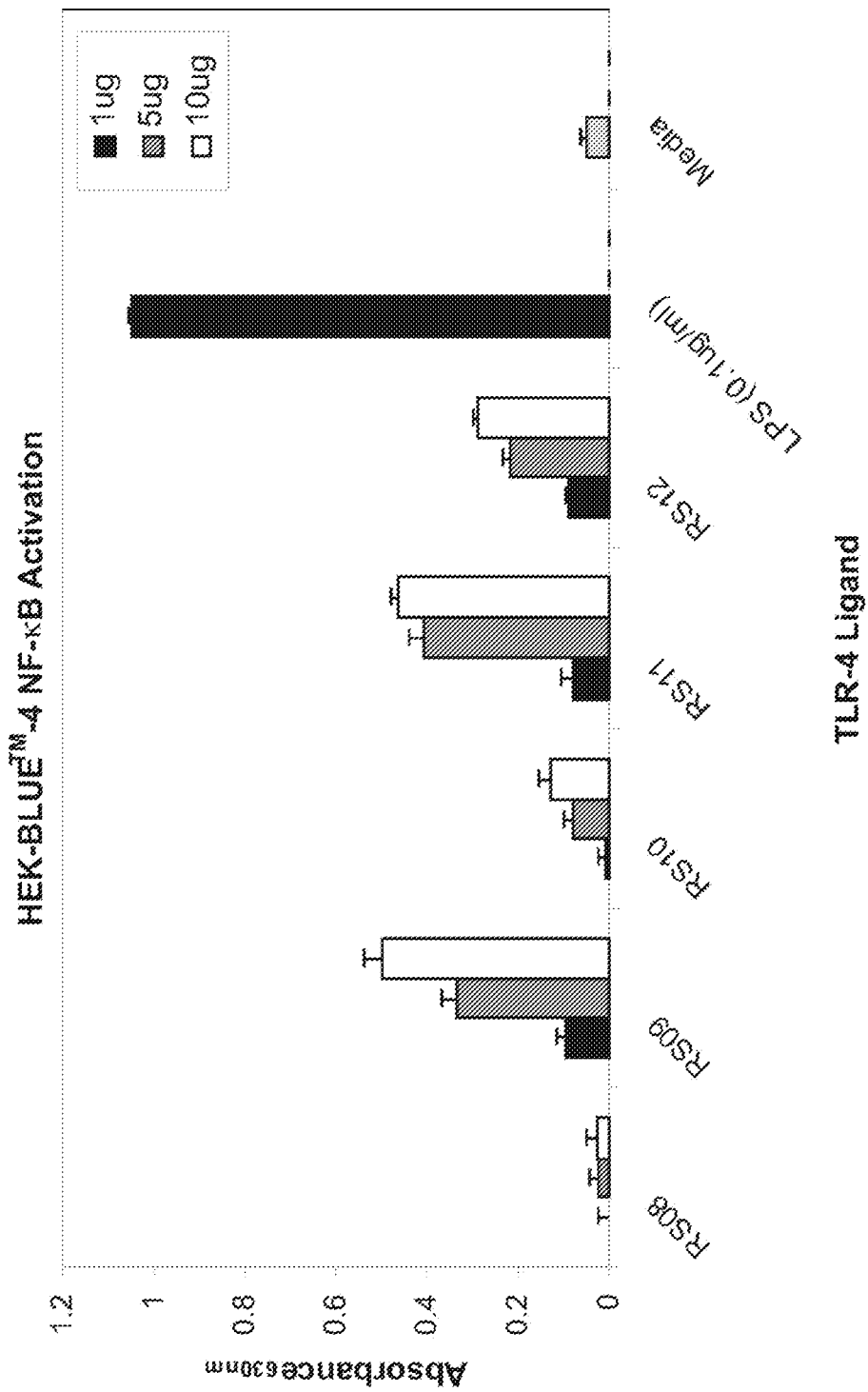

For all peptides, three concentrations, 1 μg/ml (black bars), 5 μg/ml (gray bars), and 10 μg/ml (white bars) were used to activate HEK-BLUE™-4 cells. LPS (0.1 μg/ml) was used as a positive control. Normal media was used as a negative control to assure that it did not contain any substances, such as endogenous alkaline phosphatases, which could be detected by the assay. DMSO was used as a control for peptide RS04 which was not water soluble (FIG. 2A). Of the seven peptides shown in FIG. 2A, Peptides RS01, RS03, and RS04 were considered as TLR-4 stimulating and hence activators of NF-κB. The activity of peptides RS08-RS 12 is shown in FIG. 2B in which peptides RS09, RS11, and RS 12 were considered as positive for TLR-4 stimulation and NF-κB activation.

Example 3

LPS Peptide Mimics Induce Nuclear Localization of NF-κB

LPS binding to TLR-4 results in nuclear localization of the transcription factor NF-κB, which upon binding to its promoter, results in transcription of inflammatory cytokines.

For NF-KB nuclear translocation western blots, cytoplasmic and nuclear protein extracts were prepared from HEK-BLUE™-4, HEK293, and RAW264.7 cells (2×106 cells) using NE-PER, nuclear and cytoplasmic extraction reagent kit (PIERCE, Rockford, Ill.). The manufacturer's protocol was followed to separate cytoplasmic and nuclear fractions. Nuclear and cytoplasmic lysates (10 μg protein) were subjected to 12% SDS-PAGE under reducing conditions (presence of β-mercaptoethanol). Briefly, the proteins were transferred to Immobilon-P membranes (Millipore, Billerica, Mass.) at 220 mA for 2 h and membranes were blocked with 4% dried milk in TBST [200 mM Tris-HCl, pH 7.4, 150 mM NaCl, and 0.1% TWEEN® 20 added fresh/liter of 1xTBS (TBST)] for at least 2-3 h on a shaker at room temperature. Subsequently, the membranes were incubated overnight at 4° C. with either NF-KB p65 (Cell Signaling Technology, Danvers, Mass.), IκB-α (Cell Signaling Technology), actin (Santa Cruz Biotechnology, Santa Cruz, Calif.), or HDACI (Santa Cruz Biotechnology) antibodies in TBST on a shaker. Membranes were washed three times with TBST and then incubated with the respective secondary antibody for 2 hrs at room temperature on a shaker. After four washes with TBST and one wash with TBS, membranes were developed by ECL (Pierce) and detected on HyBlot CL™ autoradiography film (Denville Scientific, Inc, Metuchen, N.J.).

NF-κB nuclear translocation was also detected by immunofluorescence.

HEK-BLUE™-4 and RAW264.7 cells were seeded in 8-chamber slides (BD Biosciences, Bedford, Mass.) at a density of 2×104 cells per well. Cells were allowed to adhere at 37° C. over night after which the cells were stimulated with LPS peptide mimics at various time points and subsequently processed for immunofluorescence. The cells were fixed with a 4% paraformaldehyde/PBS solution, followed by permeabilization with 0.2% TRITON® X-100, and blocked using a solution of 0.1% TRITON® X-100, 1% BSA, and 10% goat serum. The cells were then incubated with the NF-κB p65 antibody (1:50) (Cell Signaling) overnight at 4° C. followed by incubation for 45 min at room temperature with Alexa Fluor® 488 labeled goat anti-rabbit (1:250) (Invitrogen, Carlsbad, Calif.). The slides were then mounted with Vectashield® containing DAPI (Vector Laboratories, Burlingame, Calif.). Cells were visualized using the Axiovert 200 M microscope (Zeiss, Thornwood, N.Y.).

Figure 3A:
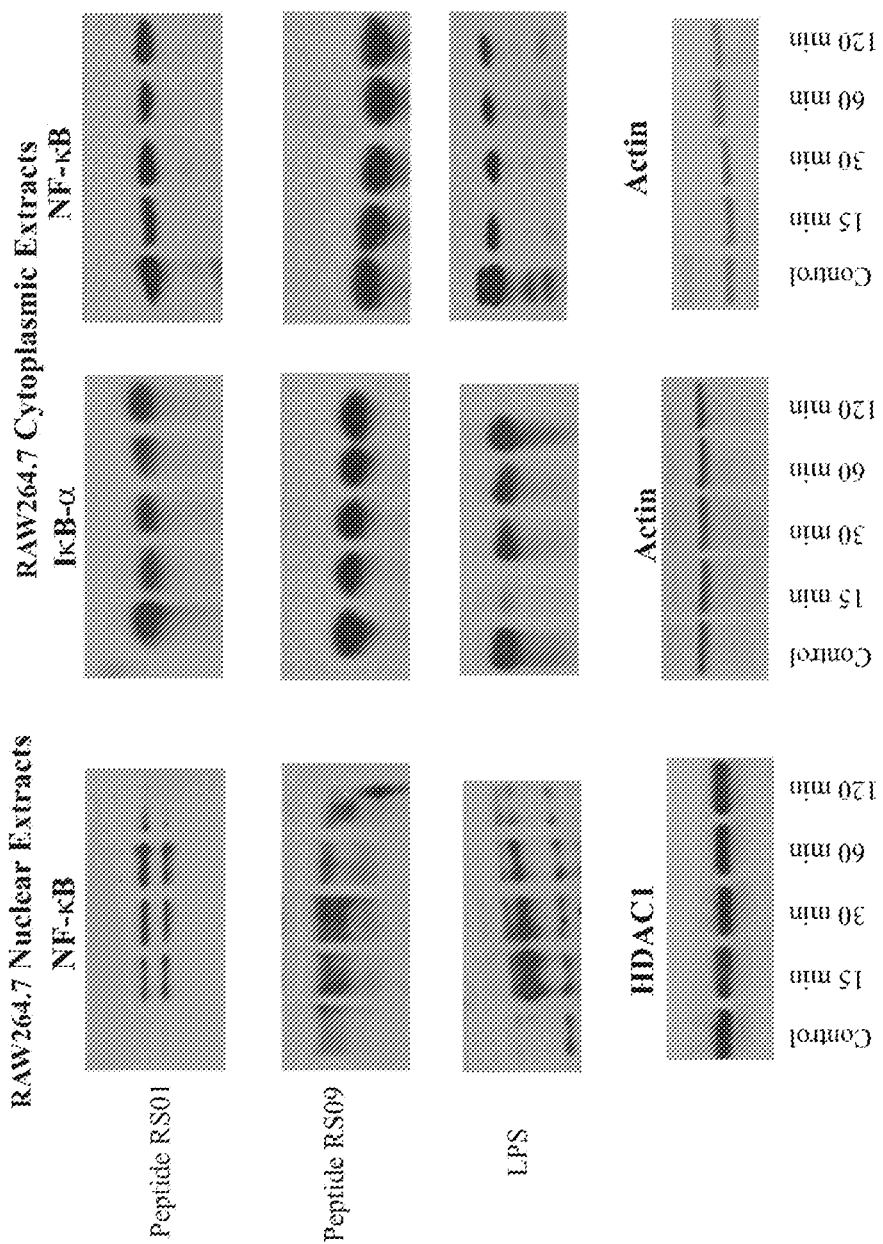
FIG. 3—LPS peptide mimics lead to NF-κB nuclear translocation. Nuclear translocation studies of NF-κB were performed by Western blot analysis on both RAW264.7 (FIG. 3A), HEK-BLUE™-4 (FIG. 3B), and HEK293 (FIG. 3C) cells. Cells were stimulated with peptide, either RS01 or RS09, at a concentration of 5 µg/ml per $5\times10^4$ cells at various time points (15, 30, 60, and 120 min) Nuclear protein fractions were assayed for NF-κB while cytoplasmic proteins fractions were assayed for both NF-κB and IκB-α. HDAC was used as a nuclear protein loading control and actin was used as a cytoplasmic protein loading control. For HEK293 cells, no differences in the levels of cytoplasmic and nuclear NF-κB were observed, suggesting that LPS, RS01, and RS09 do not activate the non-TLR-4 expressing HEK293 cells (FIG. 3C).
Figure 3B:
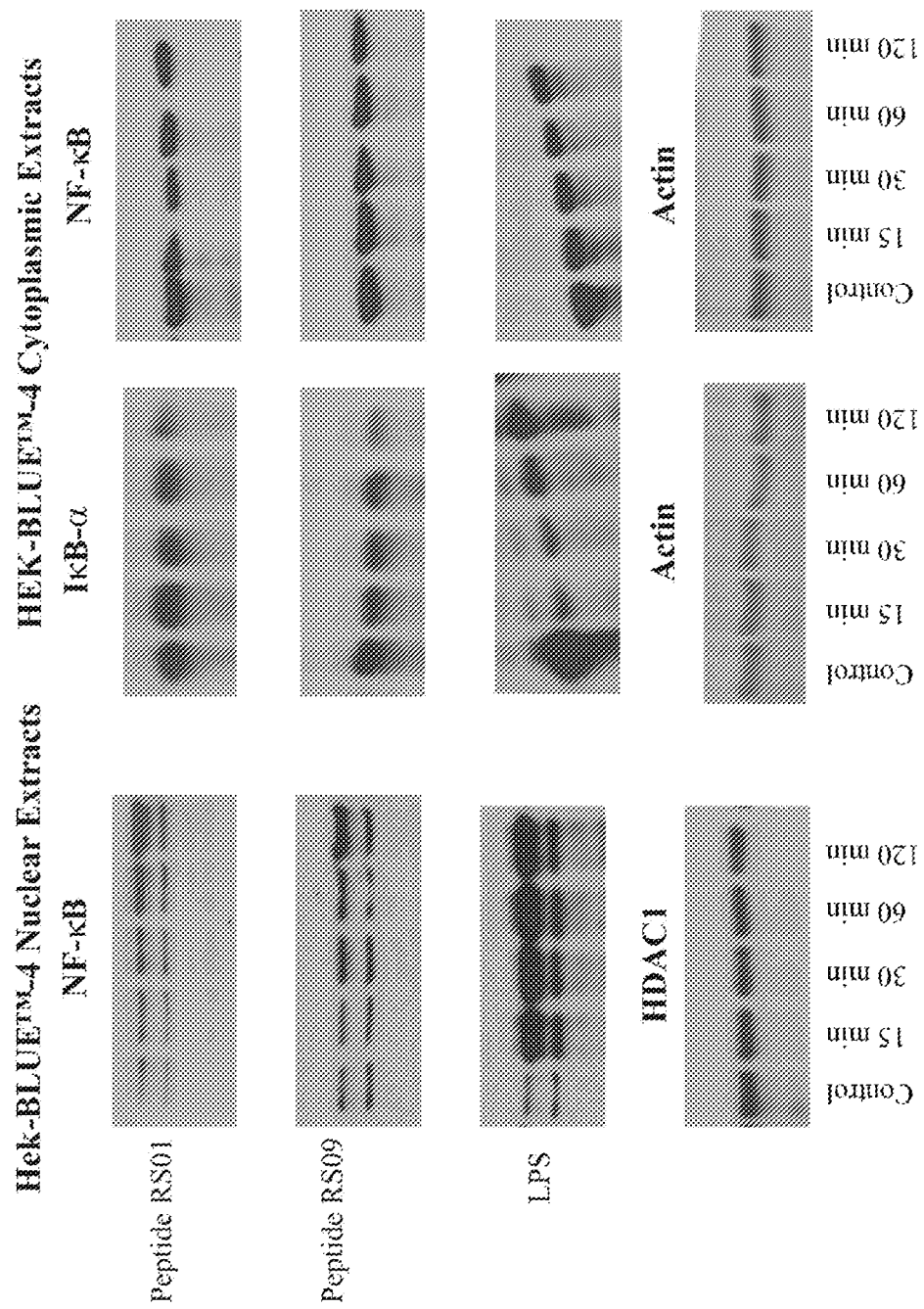
Figure 3C:
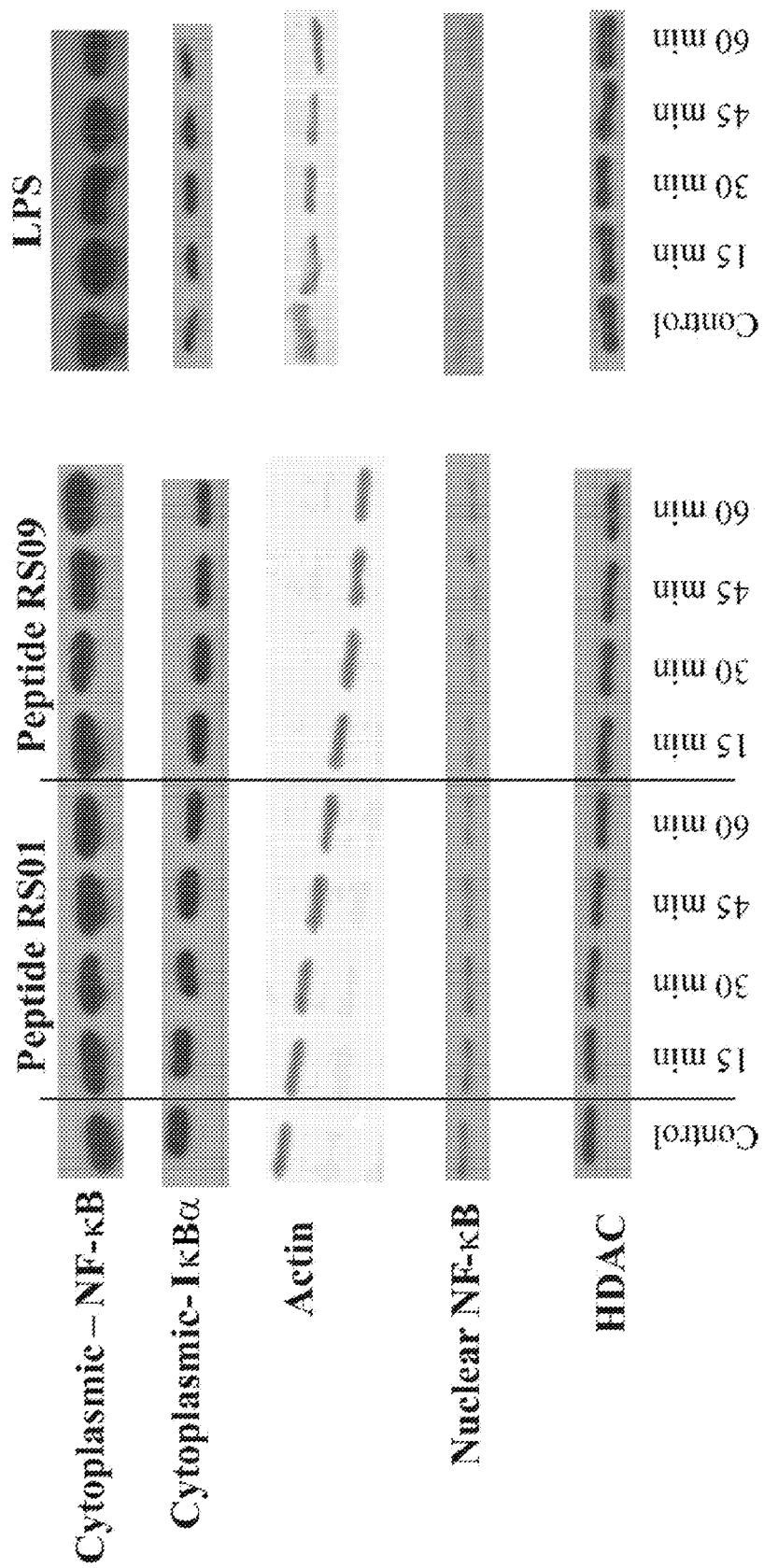
Figure 4:
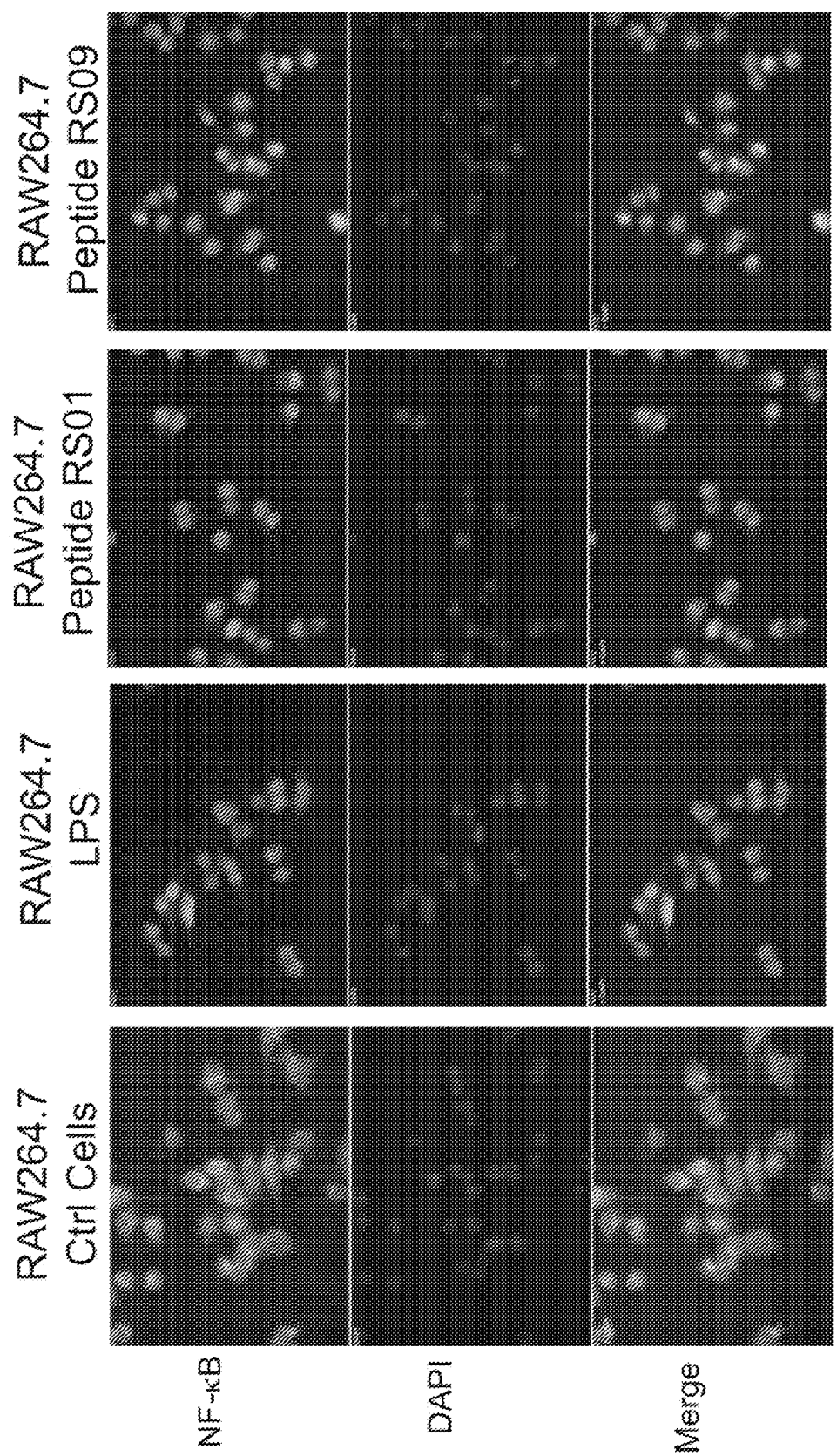
FIG. 4—Fluorescence microscopy of NF-κB nuclear translocation. RAW264.7 macrophages were seeded in 8 well chamber slides at a density of 2×104 cells per well and stimulated with 5 µg/ml of either RS01 or RS09. After 30 min incubation, cells were fixed (4% para-formaldehyde), permeabilized (0.2% TRITON® X-100), blocked (10% goat serum/1% BSA), and incubated with anti-NF-κB followed by DAPI staining of nuclei. The stained cells were visualized using the Axiovert 200 M microscope with a 40× magnification. NF-KB (green) was more diffusely spread throughout the cytoplasm in control cells but appeared more circular in RS01, RS09, and LPS treated cells. Upon merging green NF-KB with DAPI nuclei, nuclear localization of NF-κB was observed in treated but not in control cells.

Two peptides identified by phage display, RS01 and RS09, were tested for binding to TLR-4 and nuclear localization of NF-κB in the macrophage cell line RAW264.7. Nuclear localization was also assayed in HEK-BLUE™-4 cells side by side with RAW264.7 as a comparison. Both RAW264.7 and HEK-BLUE™-4 cells were incubated with either RS01 or RS09 followed by processing the cells for both cytoplasmic and nuclear protein fractions. LPS was used as a positive control for both cell lines. In RAW264.7, nuclear NF-κB was absent in non-stimulated cells and increased during the indicated times of 15, 30, 60, and 120 min (FIG. 3A). In an inactivated state, NF-κB is sequestered within the cytoplasm by IKB-α, which becomes ubiquinated and degraded upon cellular activation thus releasing NF-κB for nuclear transit. Western blot analysis demonstrated that as nuclear translocation of NF-κB increases over time, so too does the degradation of IKB-α, within the cytoplasm. Concentrations of cytoplasmic NF-κB also decrease, indicating shuttling of NF-κB to within the nucleus. Similar results pertaining to increased nuclear localization of NF-κB with simultaneous decrease of cytoplasmic IKB-a and NF-KB were observed with HEK-BLUE™4 cells (FIG. 3B). For nuclear protein extracts, histone deacetylase I (HDACI) was used as a loading control and for cytoplasmic protein extracts, actin was used as a loading control (FIGS. 3A and 3B). To demonstrate that RS01 and RS09 indeed bind to TLR-4 leading to NF-κB activation, non-TLR-4 expressing HEK293 cells were used as a negative control. No differences in the levels of NF-κB were observed within the cytoplasm and nucleus suggesting that HEK293 cells treated with either LPS, RS01, or RS09 did not result in nuclear translocation due to the lack of TLR-4 (FIG. 3C). To further demonstrate activation and nuclear translocation of NF-κB in RAW264.7, fluorescence microscopy was performed with peptides RS01 and RS09, with LPS being used as a positive control (FIG. 4). NF-κB in control cells was located within the cytoplasm as observed by the diffuse green staining cells which are better visualized upon the merge with the DAPI stained blue nucleus. When comparing LPS, RS01, and RS09 stimulated RAW264.7 cells, the green staining NF-κB appeared more rounded and not diffuse as in the control cells indicating nuclear localization, which was confirmed by merging the image with an image of DAPI stained nucleus (FIG. 4).

Example 4

LPS Mimics Activate RAW264.7 Macrophages to Secrete Inflammatory Cytokines

Inflammation results from binding of nuclear NF-κB to its promoter, initiating transcription of various cytokines. An antibody array membrane was used to determine which cytokines/chemokines were secreted in response to the LPS peptide mimics RS01 and RS09.

RAW264. 7 cells were seeded at a density of $1 \times 10^6$ cells per well of a six well plate and allowed to adhere overnight at 37° C. Cells were then stimulated with LPS peptide mimics for 24 h at 37° C. after which the cell culture supernatant was collected and assayed for various secreted inflammatory cytokines by using the mouse inflammation antibody array-1 kit (RayBio®, Norcross, Ga.). The membranes provided were blocked with 1× assay diluent followed by incubation with the cell culture supernatant overnight at 4° C. The blots were the incubated with biotin labeled anti-cytokines followed by incubation with avidin-HRP (1:250). The blots were then developed using ECL (Pierce) and detected on HyBlot CL™ autoradiography film (Denville Scientific). Detailed instructions for detection of inflammatory cytokines were provided by the manufacturer.

Figure 5A:
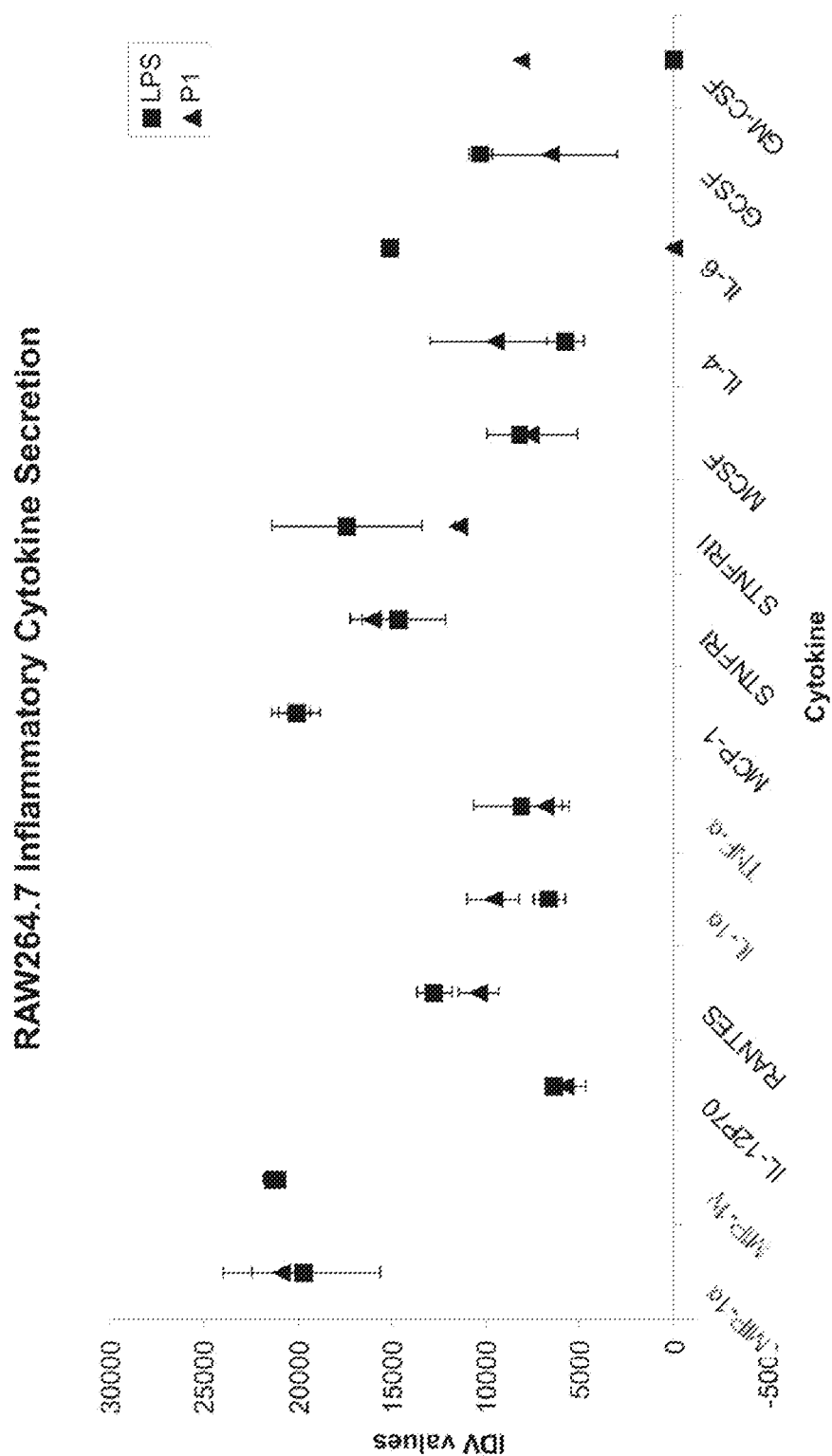
FIG. 5—RAW264.7 secretes inflammatory cytokines in response to RS01 and RS09. RAW264.7 cells were seeded at a density of $1\times10^6$ cells per well of a six well plate followed by addition of either RS10 (FIG. 5A) or RS09 (FIG. 5B) and incubated for 24 h after which the culture media was collected. LPS was used as a positive control for both RS01 and RS09. Culture media was then analyzed for specific cytokines using an antibody array kit. Both RS01 (triangle) and LPS (square) were capable of inducing inflammatory cytokines and chemokines from RAW264.7. Each cytokine is represented as an IDV value which was calculated by comparing the density of each spot with respect to the density of the internal positive controls. The antibody array represents a qualitative comparison of each cytokine and is not qualitative. Each experiment was repeated three times with similar results observed. The standard deviation shown above each sample represents three replicates in one experiment.
Figure 5B:
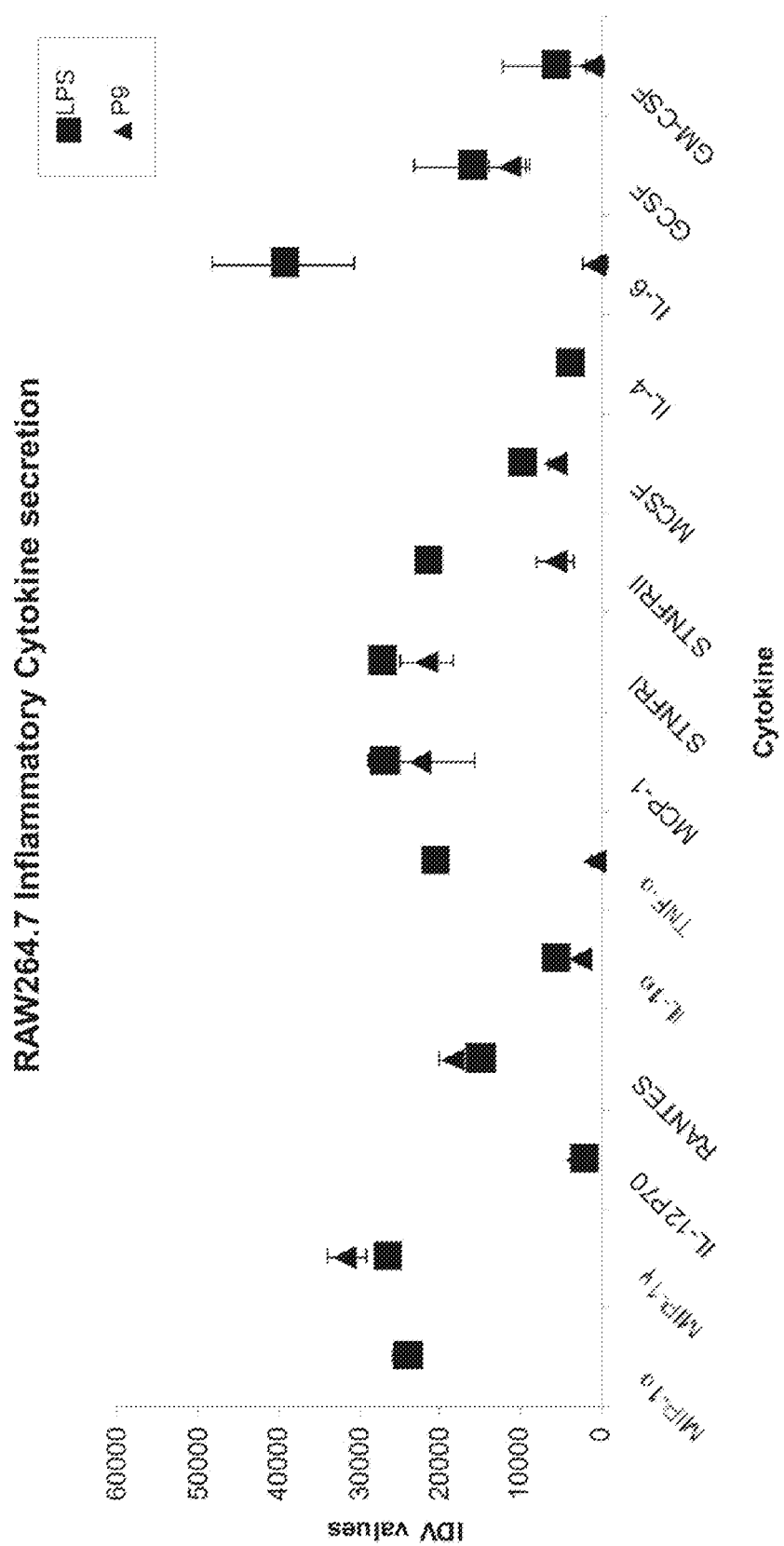

Although the values obtained for each cytokine are not quantitative but rather qualitative, they do show an increase in release of inflammatory cytokines. These values were calculated and presented as IDV, which is the density of each spot compared to the density of the internal positive controls present on each membrane. Values for the various cytokines and chemokines detected are presented in FIG. 5A for RS01 and FIG. 5B for RS09. Square boxes represent cytokines secreted upon LPS stimulation and triangles represent cytokines secreted upon peptide RS01 or RS09 stimulation. Both peptides were capable of inducing secretion of inflammatory cytokines and chemokines from RAW264.7 cells, which was comparable to those secreted from LPS stimulated cells.

Example 5

LPS Peptide Mimics Function as Adjuvants In Vivo

Weakly or non-immunogenic antigens require an adjuvant that can activate the innate immune system and subsequently initiate an antigen specific immune response. The RS01 and RS09 peptides were tested for adjuvant function in vivo. The antigen used for the in vivo adjuvant study is a 15-mer peptide (GQWQSGDRYWMETST; SEQ ID NO:13), known as X-15, which has been observed to possess prostate tumor protective properties in vivo when administered with an adjuvant.

Eight week old male BALB/c mice (Charles River Laboratories, Wilmington, Mass.) were divided into 4 groups (3 mice per group). The X-15 peptide was conjugated to Keyhole Limpet Hemocyanin (KLH) (Pierce) and injected subcutaneously. All the mice were vaccinated with 100 µg of X-15, conjugated to KLH, on day 0 and received a booster of 50 µg of X-15 conjugated to KLH, on day 14. The difference between groups was the adjuvant used, which was alum, RS01, or RS09. Alum was added at a 1:1 (v:v) ratio to X-15-KLH•while both RS01 and RS09 were added at a concentration of 25 µg. OVA peptide (8-mer peptide) served as a negative non-adjuvant peptide control and also used at a concentration of 25 µg. Blood was collected on days 0, 14, and 28.

X-15 specific antibodies in serum were determined via ELISA. X-15 peptide was resuspended in a solution of 0.25% glutaraldehyde-PBS and 5 µg peptide/100 µl was added to each well of a 96 well microtiter plate and incubated overnight at 4° C. The plates were washed with PBST (phosphate-buffered saline with 0.05% TWEEN® 20) three times and then wells blocked with 5% milk-PBS for 2 h at room temperature. The plates were washed with PBST once. Then, 100 µl of mouse sera was added at the given dilution (1:200) and incubated at room temperature for 2 h. The plates were then washed with PBST four times and 100 µl of horse radish peroxidase (HRP) labeled anti-mouse IgG (1:5000 in 2% milk) was added to each well for 1 h at room temperature. The plates were washed five times with PBST and developed by adding 100 µl of the HRP substrate, OPD-hydrogen peroxide (Sigma). The reaction was stopped by adding 50 µg of 4N H2S04 and the absorbency was taken at 490 nm and referenced at 405 nm.

Figure 6:
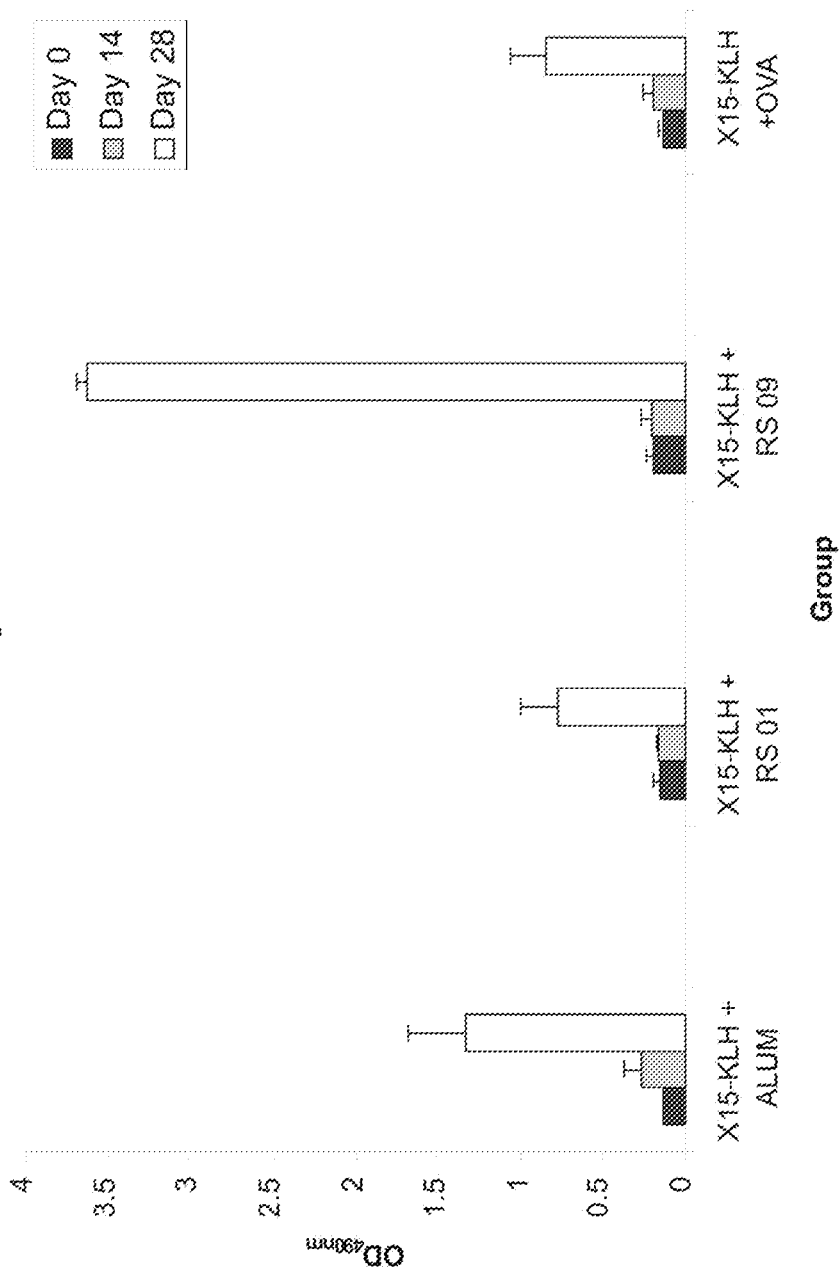
FIG. 6—RS09 functions as an adjuvant in vivo. Four groups of mice (3 mice/group) were vaccinated with X-15 (100 µg) conjugated to KLH. The mice were bled on days 0, 14, and 28. The serum obtained from each animal was analyzed for presence of X-15 specific antibodies by direct ELISA with immobilized X-15 peptide. The difference between groups was the adjuvant used, which was Alum, RS01 or RS09. OVA peptide (8-mer peptide) was used as a negative peptide control. The highest X-15 specific antibody concentration was observed on Day 28 post vaccination (white bars) for all groups. RS09 significantly enhanced the X-15 specific antibody response on day 28. The standard deviation represents triplicate values for each group of animals.

Serum X-15 specific antibody concentrations are shown in FIG. 6. RS09 produced a robust X-15 antibody response in vivo, compared to alum and RS01. This significant increase in X-15 specific antibody concentration with RS09 was observed on day 28 (white bar) post vaccination as shown in FIG. 6. RS01 and RS09 were given at a concentration of 25 µg for the initial vaccination on day 0 and for the booster on day 14. The 25 µg starting dose dose does not induce an antibody response to the adjuvant, and hence is nonimmunogenic. To confirm this observation, two groups of 3 mice were vaccinated with either 25 ng of RS01 or RS09 and no antibodies were produced in these mice (data not shown). Thus, while RS01 and RS09 were not immunogenic at the concentration used, RS09 was capable of enhancing production of X-15 specific antibodies.

What is claimed is:

1. A method of identifying an immunological adjuvant, the method comprising isolating a peptide that binds specifically to an anti-lipopolysaccharide core antibody or an antigen binding fragment thereof, stimulates toll-like receptor-4 (TLR-4) and activates the NF-kB in a cell, wherein the peptide is 7 to 15 amino acids in length and wherein the stimulation of the toll-like receptor-4 (TLR-4) and the activation of the NF-kB identify the peptide as an immunological adjuvant.

2. The method of claim 1, wherein the antibody is 2D7/1.

3. The method of claim 1, wherein the activation of the NF-kB is indicated by nuclear localization of the NF-kB in the cell.

4. The method of claim 1, wherein the activation of the NF-kB is indicated by secretion of one or more inflammatory cytokines from an antigen presenting cell.

5. The method of claim 4, wherein the antigen presenting cell is a macrophage.

6. The method of claim 1, wherein the peptide is identified by screening a phage display library.

7. The method of claim 1, wherein the peptide is SEQ ID NO: 1 or SEQ ID NO: 9.

\* \* \* \* \*